United States Patent [19]

Athanasiou et al.

[11] Patent Number: 5,607,474
[45] Date of Patent: Mar. 4, 1997

[54] MULTI-PHASE BIOERODIBLE IMPLANT/CARRIER AND METHOD OF MANUFACTURING AND USING SAME

[75] Inventors: Kyriacos A. Athanasiou, Helotes; Barbara D. Boyan, San Antonio, both of Tex.

[73] Assignee: Board of Regents, University of Texas System, Austin, Tex.

[21] Appl. No.: 123,812

[22] Filed: Sep. 20, 1993

Related U.S. Application Data

[63] Continuation of Ser. No. 837,401, Feb. 14, 1992, abandoned.

[51] Int. Cl.⁶ .................................. A61F 2/24; A61F 2/28
[52] U.S. Cl. ............................ 623/11; 623/16; 623/66
[58] Field of Search .............................. 623/1, 2, 11, 12, 623/16, 18, 66; 606/151, 152, 153, 154, 155; 600/29, 30, 32

[56] References Cited

U.S. PATENT DOCUMENTS

| | | | |
|---|---|---|---|
| 3,620,218 | 11/1971 | Schmitt | 606/154 |
| 3,739,773 | 6/1973 | Schmitt et al. | 606/77 |
| 4,246,709 | 1/1981 | Schmitt . | |
| 4,261,969 | 4/1981 | Heller . | |
| 4,460,562 | 7/1984 | Keith et al. . | |
| 4,532,123 | 7/1985 | Gardner . | |
| 4,650,488 | 3/1987 | Bay et al. | 623/11 |
| 4,652,264 | 3/1987 | Dumican | 623/11 |
| 4,705,039 | 11/1987 | Sakaguchi et al. | 606/154 |
| 4,756,862 | 7/1988 | Spector et al. | 623/11 |
| 4,968,317 | 11/1990 | Tormala et al. | 606/77 |
| 4,997,440 | 3/1991 | Dumican | 623/11 |
| 5,084,051 | 1/1992 | Tormala et al. | 606/77 |
| 5,133,754 | 7/1992 | Laghi | 623/11 |
| 5,206,023 | 4/1993 | Hunziker . | |
| 5,270,300 | 12/1993 | Hunziker . | |
| 5,306,311 | 4/1994 | Stone et al. | 623/18 |

FOREIGN PATENT DOCUMENTS

| | | | |
|---|---|---|---|
| 0326426 | 8/1989 | European Pat. Off. | 623/11 |
| 1745676 | 7/1970 | Germany | 623/11 |

OTHER PUBLICATIONS

Robert Langer, "Controlled Release: A New Approach to Drug Delivery" *Technology Review*, pp. 26–34, Apr. 1981.

D.F. Williams, "Some Observations on the Role of Cellular Enzymes in the In-Vivo Degradation of Polymers", *Corrosion and Degradation of Implant Materials, ASTM STP* 684, B.C. Syrett and A. Acharya, Eds., American Society for Testing and Materials, 1979, pp. 61–75.

"Bone Regeneration Materials For The Mandibular And Craniofacial Complex", Hollinger et al., vol. 2, No. 2, (1992) (pp. 143–151).

*Primary Examiner*—David Isabella
*Attorney, Agent, or Firm*—Greenlee and Winner

[57] ABSTRACT

A carrier and method of manufacturing and using the same is provided for receiving supporting replenished tissue growing into a diseased or damaged area within a physiological system. The carrier can be implanted in the interface region between tissue having different mechanical properties to support the growth and regeneration of differing types of tissue within the region. The carrier includes bioerodible polymeric material having differing mechanical properties such as porosity, stiffness and compressibility.

20 Claims, 3 Drawing Sheets

MULTI-PHASE BIOERODIBLE IMPLANT/CARRIER AND METHOD OF MANUFACTURING AND USING SAME

Research leading to the present invention was supported in part by NIH grant UTHSCSA:K-GASO-30-904-2-16. The government therefore has certain rights in the invention.

This application is a continuation of application Ser. No. 07/837,401 filed Feb. 14, 1992, now abandoned.

BACKGROUND OF THE INVENTION

1. Field of the Invention

This invention relates to a multi-phase biodegradable implant/carrier (carrier) and a method for manufacturing and using the carrier in a physiological system to receive, induce and support subdermal tissue.

2. Description of Relevant Art

Devices used for treating and repairing damaged or defective tissue are well-known in the art. Whenever damage to tissue occurs, the tissue must be supported in a fairly stable condition as it is being regrown. Some structural types of tissue such as bone can be regrown naturally provided the trauma area is not significantly disrupted during the healing process. Outer supports such as a cast or sling can be used to secure the trauma area. Inner supports such as rods or pins may also be used in severe cases.

If the damaged tissue region has low cellular density or lacks vasculature, as in articular cartilage, the healing process can sometimes last several months, years or may not occur whatsoever. If inner support pins are used, they require surgical implantation and, after several months or years, the pins often need to be surgically removed. Surgically implanting and removing support pins presents undue shock or trauma to the patient's system. Moreover, once the internal supports are removed, a hole or void is left in the region which must then be naturally filled with growing tissue to fully complete the healing process. In the interim, the hole or void may leave the tissue prone to subsequent damage or breakage.

SUMMARY OF THE INVENTION

The problems outlined above are in large part solved by the carrier of the present invention. That is, the carrier hereof provides convenient access for tissue ingrowth into and within the carrier's body. These sites allow tissue to invade the carrier's outer surface through growth channels (pores). These pores exist for promoting and receiving regenerated or resurfaced tissue. The carrier of the present invention can be implanted into a physiological system at a location adjoining two dissimilar types of tissue, e.g., cartilage and bone. The carrier of the present invention may also be implanted in other types of support or vascular tissues, e.g., at ligament and tendon insertion sites, in growth plate, at the periosteum-bone interface, and in hyaline cartilage and adjacent tissues, etc.

The tissue carrier of the present invention includes bioerodible polymeric material which substantially or completely dissolves over a period of time when exposed to aqueous fluids. During the time in which the carrier dissolves, growing tissue enters the access locations thereby providing a "scaffold" into which rapid tissue regeneration can occur in the damaged or diseased area. The carrier is particularly appropriate for promoting healing in tissue areas which do not heal easily. The dissolvable carrier provides interim support to the tissue area while tissue is being regenerated. Accordingly, the carrier of the present invention presents a bioerodible scaffold-type network for promoting, supporting and receiving the regeneration of diseased or damaged tissue. Thus the patient is not subjected to undue trauma or risk associated with conventional internal rods or pins, or other non-degradable materials. In addition, wounds which would otherwise not heal with normal tissue are able to do so.

Broadly speaking, one embodiment of the present invention contemplates a carrier comprising at least two bioerodible polymeric materials having dissimilar mechanical properties arranged proximate to each other. The two bioerodible polymeric materials are capable of being placed into a physiological system adjoining two dissimilar types of tissue. Each polymeric material may also include an enzyme or other agents which may enhance material degradation. The carrier may also contain one or more growth factors, or other agents, which promote differentiation and growth of normal tissue. Enzymes, growth factors or other agents in one material can be mixed in different proportion to these additives in the other material to produce differing amounts of bioerosion or tissue repair depending upon the application desired. Each polymeric material has a variable degree of porosity or pore sizes into which tissue can enter and possibly adhere temporarily.

In another embodiment, the carrier of the present invention is capable of being subdermally implanted as a tissue support system. Preferably, the carrier can be implanted at an interface region between two dissimilar types of tissue. At least a portion of the carrier includes a first material having access sites for receiving growth of a first type of tissue. In addition, the carrier includes a second material having access sites for receiving growth of a second type of tissue. Once the carrier is implanted, the first material resides substantially within the first type of tissue and the second material resides substantially within the second type of tissue. According to one aspect of the invention, access sites within the first material comprise pores extending into and within the first material and access sites within the second material comprise pores extending into and within the second material.

The present invention also contemplates a method for implanting a carrier within a physiological system including a bioerodible carrier having a first bioerodible polymeric material bonded to a second bioerodible polymeric material. For example, in the case of articular cartilage and bone, a hole may be bored through skin, underlying cartilage and into a bone thereby providing a passage into which the carrier can be implanted. Once placed, the first material of the carrier resides substantially within the bone and the second material resides substantially within the cartilage. The skin can be sutured over the carrier to prevent infection from entering the tissue area.

The present invention additionally contemplates a method for manufacturing a bioerodible carrier comprising solubilizing a polymer into a viscous form and then extracting substantial amounts of solvents from the viscous polymer to form pores within the resulting modified polymer. Internal pores within the modified polymer provide access locations along the outer surface of the carrier. A plurality of larger passages can also be mechanically placed within the modified polymer to increase the number of access locations. A second modified polymer can be added to a first modified polymer by bonding together the first and second polymers within a mold subjected to pressure-curing. Additional modified polymers can also be added.

BRIEF DESCRIPTION OF THE DRAWINGS

Other features and advantages of the invention will become apparent upon reading the following detailed description and upon reference to the accompanying drawings in which.

Figure 1:
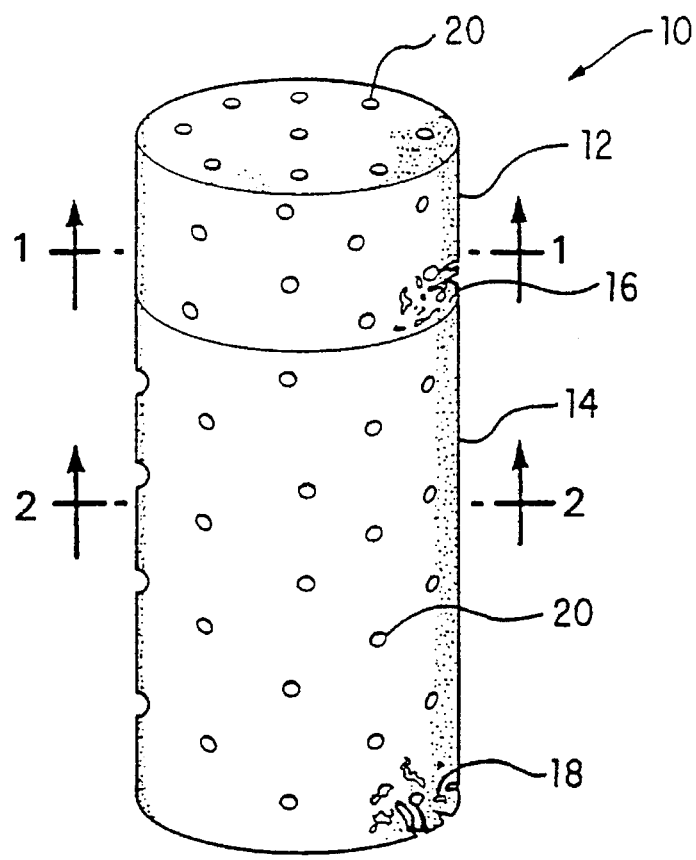
FIG. 1 is a perspective view of a two-phase carrier according to the present invention.

While the invention is susceptible to various modifications and alternative forms, a specific embodiment thereof has been shown by way of example in the drawings and will herein be described in detail. It should be understood, however, that the drawings are not intended to limit the invention to the particular form disclosed, but on the contrary, the intention is to cover all modifications, equivalents and alternatives falling within the spirit and scope of the invention as defined by the pending claims.

DETAILED DESCRIPTION OF THE INVENTION

Turning now to the drawings, a carrier 10 is illustrated in FIG. 1 comprising a first bioerodible polymeric material 14 and a second bioerodible polymeric material 12. First material 14 and second material 12 are preferably made from a copolymer-based material of polyglycolic acid (PLG) and polylactic acid (PLA) in a 50/50 concentration of each. Also present in the PLA/PLG copolymer material may be an enzyme homogeneously dispersed within the copolymer which may enhance the degradation of the polymeric substance. Degradable polymeric substances useable in the present invention are frequently found in the general categories commonly known as polyesters, polyamides, polypeptides, or polysaccharides. Certain typical enzyme-degradable polymeric substances have long been used as biodegradable materials for sutures, for example. These typical degradable materials include alkylhydroxylic acids including, for example, the polyesters of monomeric units such as lactic acid, glycolic acid, hydroxypropionic acid, hydroxybutyric acid and combinations thereof. Lactic acid and glycolic acid are most commonly used for this purpose and preferably used in the present invention. Polymer of lactic acid (PLA) and glycolic acid (PGA) are well known in the art as described in U.S. Pat. No. 3,991,776 (herein incorporated by reference).

Enzymes useable in the practice of the present invention are of a wide variety but most frequently are proteases or hydrolases with ester-hydrolyzing capabilities. Such enzymes include proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase or an oxidase.

The ability of naturally occurring enzymes to degrade polymeric substances or materials are known in the art. See, e.g., Williams, D. F., "Some Observations on the Role of Cellular Enzymes in the In-Vivo Degradation of Polymers," *Corrosion and Degradation of Implant Materials*, ASTM STB 684, American Society for Testing and Materials, 1979, pp. 61–75.

A ratio of 50% PLA and 50% PLG suitable for materials 12 and 14 of the present invention can also be implanted with growth factors (e.g., transforming growth factor-beta) or other forms of therapeutic agents such as steroids or hormones for actively increasing the growth rate of the tissue area into which carrier 10 is capable of being placed. Dispersing therapeutic agents within a polymeric material is known in the art and generally described by Langer, R., "Controlled Release: A New Approach to Drug Delivery," *Technology Review*, Apr. 1981, pp.26–34. Generally speaking, the therapeutic agent is homogeneously dispersed and entrapped in the polymeric material such that release of the agent is dependent upon the rate at which fluid diffuses through the polymer material. An example of therapeutic agents erodibly released at a controlled rate to surrounding tissue is described in U.S. Pat. No. 4,346,709 (herein incorporated by reference).

Referring to FIG. 1, first material 14 is bonded to second material 12, wherein material 14 includes a body having dissimilar mechanical properties from material 12. Materials 14 and 12 may both include enzymes and therapeutic agents in addition to numerous pores 16 and 18 formed within first material 14 and second material 12, respectively. Pore size varies depending upon the process by which materials 12 and 14 are processed. Preferably, porosity within each material 12 or material 14 is more than 50% of the respective material volumetric area. Moreover, pore size can range between 50 and 200 μm. However, it is to be appreciated that pore density as well as pore size can vary outside these ranges depending upon the particular manufacturing process chosen, as described herein below. Preferably, material 12 is manufactured having a porosity which generally matches the porosity of the surrounding tissue into which carrier 10 is placed. Similarly, material 14 can be manufactured to a porosity substantially equal to its surrounding tissue. Thus, depending upon the specific application desired, the method of manufacturing carrier 10 can be quickly and easily altered to contain pores of varying size and density.

Carrier 10 can also be perforated with a plurality of passages 20 extending partially or completely through carrier 10. Passages 20 are suitably placed to provide additional sites or locations into or onto which surrounding tissue can enter and/or temporarily bond. Passages 20 are generally larger in diameter than pores 16 or 18 and can be mechanically placed as described below.

Figures 1A, 1B:
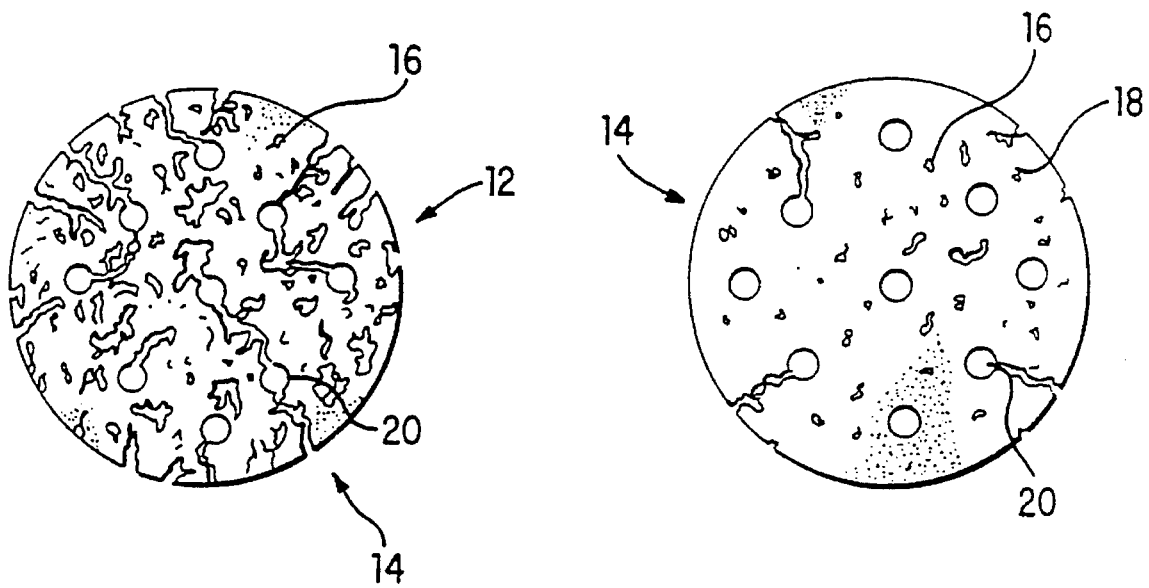
FIG. 1A is a cross-sectional view along plane 1—1 of FIG. 1.
FIG. 1B is a cross-sectional view along plane 2—2 of FIG. 1.

Referring to FIG. 1A, a cross-sectional view of material 12 is shown having numerous access sites or locations formed by pores 16 and passages 20. As shown by the comparisons of FIGS. 1A and 1B, material 14 is less porous than material 12 to substantially match a less porous tissue surrounding material 14 than the tissue surrounding material 12. Moreover, material 12 and 14 can be manufactured having mechanical properties such as stiffness and compressibility, in addition to porosity, to substantially match the mechanical properties of surrounding tissue into which material 12 and 14 is placed.

Figure 2:
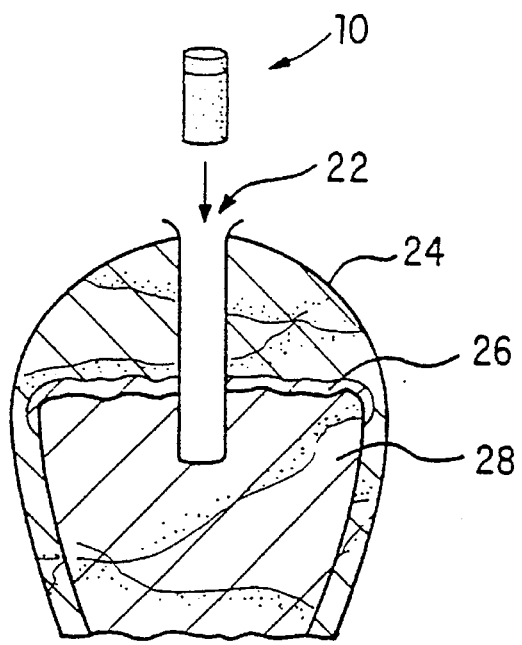
FIG. 2 is a cross-sectional view of an example of a physiological system prepared for implantation of a tissue carrier according to the present invention.

Tissue carrier 10, having materials 12 and 14 of possibly different mechanical properties, is particularly adapted for placement into a juncture region adjoining tissue areas having dissimilar mechanical properties. Materials within carrier 10 correspondingly can be processed to have mechanical properties such as porosity, stiffness, etc. to substantially match the properties of the tissue juncture region after implantation. As illustrated in FIG. 2, a physiological environment into which carrier 10 can be placed, includes, but is not limited to, a human or animal articular cartilage and underlying bone. Carrier 10 is shown insertable into a bore 22 through skin 24, through underlying cartilage 26 and into bone 28. Alternatively, carrier 10 can be placed entirely within bone 28 to provide structural support to the juncture region between cortical bone and cancellous bone. Accordingly, bore 22 and implantable carrier 10 can be placed into any physiological system having a juncture between dissimilar types of tissue. As used herein, "tissue" includes cellular material found subdermally anywhere within an animal or human anatomy. Any region joining two dissimilar types of tissue (i.e., bone, cartilage, tendon, skin, ligament, cementum, etc.) can be implanted with the bonded dissimilar materials 12 and 14 of carrier 10. By bonding each material together and implanting the combination within a tissue juncture, carrier 10 ensures the tissue juncture remains together during the repair process, which may help to promote rapid healing.

Figure 3:
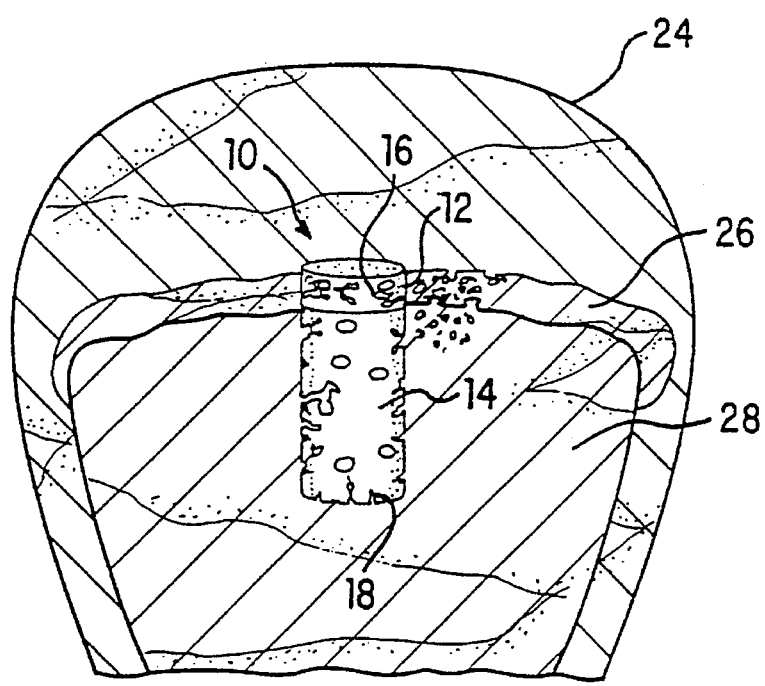
FIG. 3 is a cross-sectional view of an example of a physiological system implanted with a tissue carrier according to the present invention.

FIG. 3 illustrates carrier 10 fully implanted within dissimilar tissue regions, e.g., cartilage 26 and bone 28. After inserting carrier 10 through hole 22, outer skin 24 is sutured over the bore passage to prevent infection from entering the underlying region. As can be appreciated from the present invention, carrier 10 is produced in any desired shape with differing mechanical characteristics depending upon the size and composition of the target area. In this example, carrier 10 is cylindrical in shape having an outer diameter generally matching the inner diameter of a bore or hole 22 created in the region of interest. However, other shapes can be produced and inserted into the hole. Regardless of the shape used, the carrier can expand to match the internal cavity or bore size prior to or during the bioerodible process. Still further, the proportionate sizes of material 12 and 14 can be varied depending upon the relative location of carrier 10 in relation to the interface region. For example, cartilage 26 may be thicker than that indicated in FIG. 3 such that its thickness would be equal to or greater than the bore 22 depth into bone 28. Consequently, material 14 can be made larger or thicker than material 12 to correspond with the relative shift in boundary between cartilage 26 and bone 28.

Bone 28 generally presents a less porous and stiffer material than overlying cartilage 26. Therefore, as shown in FIG. 3, pores 18 can be made relatively smaller than pores 16. Accorded access sites or locations into pores 18 and 16 are dissimilar to generally match surrounding bone 28 and tissue 26, respectively. During the time in which bone 28 and cartilage 26 tissue regenerate and grow into the damaged region partially replaced with carrier 10 and pores 18 and 16, respectively, carrier 10 maintains a somewhat rigid support structure. As the structure of carrier 10 gradually erodes or dissolves, regeneration of tissue takes place which replaces the structural support lost during erosion. Accordingly, the present invention serves to provide better anchorage of regenerated tissue in the damaged or defective region and also provides a temporary support structure which need not be subsequently removed as in conventional rods and pins. The bioerodible carrier 10 is particularly useful in juncture regions where slow healing occurs due to lack of vasculature or cell population.

Figure 4:
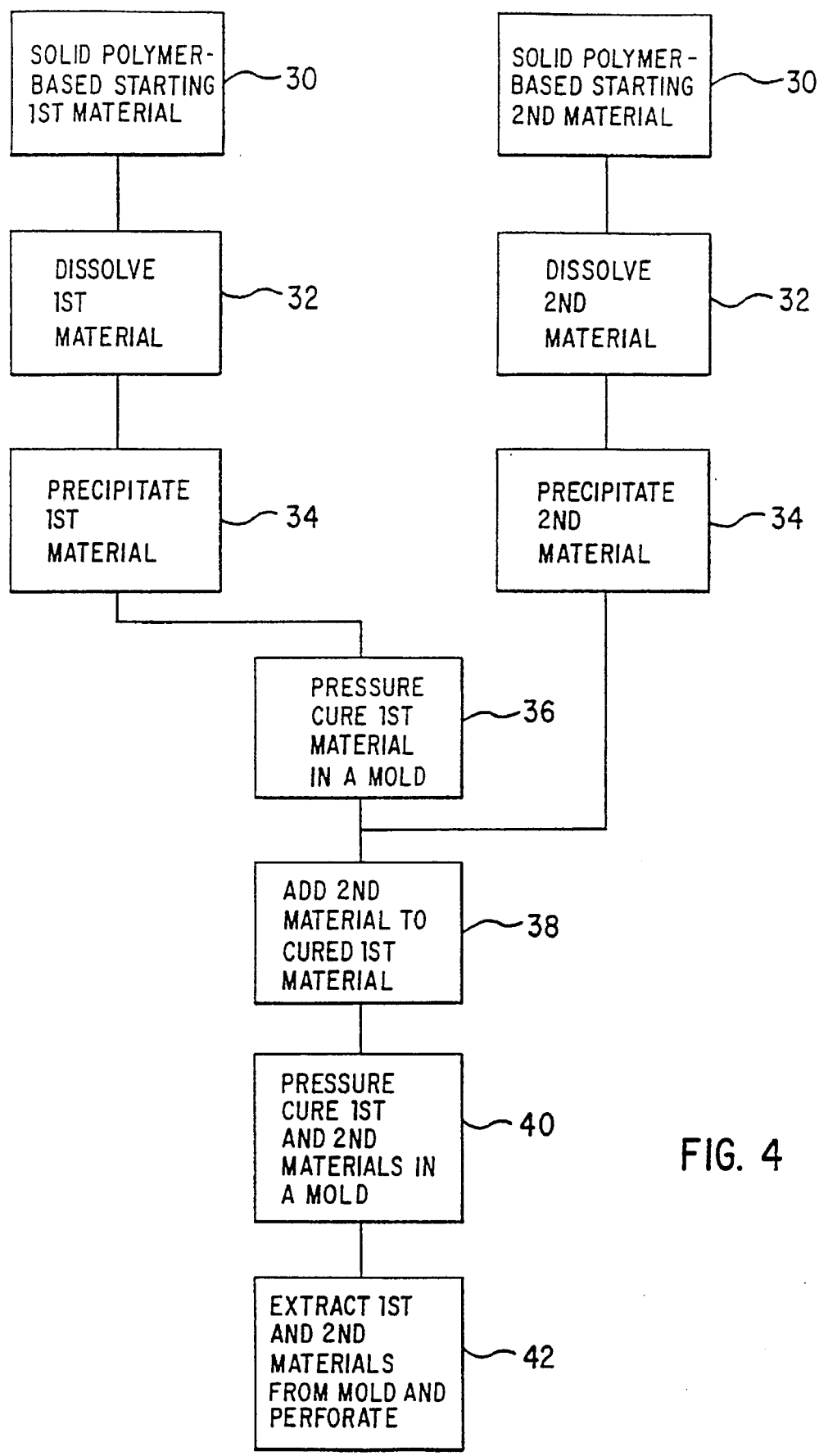
FIG. 4 is a flow diagram of steps taken to produce a two-phase carrier according to the present invention.

As illustrated in FIG. 4, the method by which carrier 10 is produced is fairly simple and does not require expensive equipment. In particular, a PLA/PLG mixture of polymer-based starting material 30 is preferably used in solid form as the starting material. The starting polymer-based solid form material may be purchased through, for example, Burmingham Polymers, Inc., Burmingham, Ala. The starting material can be placed in a mixing bowl and solubilized or dissolved 32 in a liquid such as acetone to produce a liquid form of PLA/PLG polymer. The liquid form can then be precipitated 34 with a suitable solvent such as ethanol to remove part of the liquid phase leaving a fairly viscous mixture of material. This material can be set aside and designated as first material and then the solubilized and precipitated steps 32 and 34 repeated for a second material. The first material may, for example, be used to produce material 14 and the second material used to produce material 12 as shown in FIGS. 1–3.

Depending upon the amount of porosity, stiffness or compressibility of the finished product, more or less acetone and/or ethanol can be utilized. For example, if more acetone is used, the finished product may have a higher porosity, less compressive stiffness and less resulting viscosity. If material 12 is to be placed adjacent to cartilage 26, then a suitable viscosity of the product used to form material 12 may be approximately 0.43 dl/gm (average molecular weight 12–15 kD). Conversely, if material 14 is to be placed adjacent bone, then the target viscosity of product used to form material 14 may be approximately 0.53 dl/gm (average molecular weight 60–70 kD). Depending upon the mechanical characteristics of tissue surrounding the implanted carrier 10, more or less dissolving and/or precipitating agent can be added to the starting material so that the resulting product has substantially similar mechanical characteristics to the surrounding tissue.

The resulting product receives its mechanical properties and desired porosity by placing the product in a suitable vacuum of approximately 20 m Torr for 30 minutes to help dry the material to its desired state. More or less vacuum pressure for longer or shorter periods of time can be used to increase or decrease the porosity of the material. A pressurized chamber with regulated temperature is suitable to effectively drive out most of the dissolving and precipitating agents to render the product mechanically compatible with the target tissue area into which it is capable of being placed.

Once the product has been pressurized and pores imparted within the bulk material, the material is placed into a mold. Preferably, the mold is made of a Teflon® material having one or more wells adapted to receive the material in its modified form. Each well of the mold is shaped depending upon the particular geometric configuration required of carrier 10. Either first material 14 or second material 12 is initially placed into the mold and a plug also inserted into the mold. The plug can be actuated against the material thereby compressing 36 the material between the plug and surrounding walls of the mold.

The plug can contain a plurality of elongated tines which penetrate at least partially into the material forming passages 20 which extend along the longitudinal axis of, e.g., a cylindrical carrier configuration. Duration of the compression by a plug can vary depending upon the resulting mechanical properties desired. More compression, for example, will create a less porous, less compressible material suitable for placement in heavier, denser tissue such as cortical bone, whereas less compression will produce a more porous, more compressible material suitable for placement in lighter tissue such as cartilage or ligaments. If bone is the target area into which first material 14 is placed, then pressure cure via the plug can last for approximately 48 hours in room temperature. However, the amount of cure can change drastically depending upon the mechanical properties desired.

Another batch of material or, e.g., second material 12 can be added 38 to the mold on top of and adjacent to, e.g., the first material 14. The first and second material 14 and 12 are then pressure-cured 40 via the plug having longitudinal tines placed therein. Pressure-cure can vary drastically, however, a preferred duration is approximately 48 hours, similar to the cure period of previous material. After the combination of first and second material 14 and 12 is fully cured within the mold, the resulting carrier 10 is removed or extracted 42 from the mold and perforations placed into the carrier substantially perpendicular to the passages created by the tines. A preferred method of placing the perforations or lateral passages 20 into carrier 10 would include rolling carrier 10 on a special surface which creates passages of approximately 1.5 mm in diameter.

The resulting carrier 10 includes first and second material 14 and 12 molded or bonded together in a fairly rigid, yet porous multi-phase structure which is then finally lyophilized for 48 hours at 20 m Torr and 40° C. to remove remnants of the solvents. The first material 14 will be macro- and micro-porous but may be stiffer than material 12 due to it possibly having higher molecular weight, longer curing, and higher compressibility. First material 14 preferably interfaces with a more dense tissue such as subchondral bone to provide fixation of growing bone tissue, whereas second material 12 interfaces with less dense tissue such as cartilage.

As shown in FIGS. 2 and 3, carrier 10 is insertable as a press-fit in the osteochondral defect region. The swelling characteristics of the bioerodible material 14 and 12 is expected to improve retention of carrier 10 within the defect region. Comparable mechanical properties of materials 14 and 12 to that of surrounding tissue avoids stress concentrations during joint articulation. By matching mechanical characteristics such as porosity, exchange of nutrients from the tissue into carrier 10 is provided as though normal growth patterns occur. Confocal laser scanning micrographs of carrier 10 may illustrate carrier 10 having pores 16 and 18 of varying sizes, but which are generally microporous and may be interconnected throughout the cross-sectional area of the material.

The foregoing description of the present invention has been directed to particular embodiments. It will be apparent, however, to those skilled in the art, that modifications and changes in both the carrier and the method of making and using the carrier can be made without departing from the scope and spirit of the invention. For example, curing times and pressures can vary as well as the relative concentrations of the dissolving and precipitating agents. Further, carrier 10 can be made of varying sizes and shapes depending upon the appropriate environment into which it is placed. Still further, varying amounts of enzymes or other agents can be incorporated into the polymeric material to vary the erodibility of the material depending upon the amount of healing time required. Finally, varying amounts of growth factors, hormones, or other agents, can be incorporated into the polymeric material to vary the ability of the implant to induce, promote, and support tissue in growth and repair. Therefore, it is the intention in the following claims to cover all such equivalent modifications and variations which fall within the true spirit and scope of this invention.

What is claimed:

1. A molded biodegradable polymeric implant comprising:
   a first porous layer comprising a first biodegradable polymeric material, the first layer having a predetermined porosity for receiving growth of a first type of tissue during use;
   a second porous layer comprising a second biodegradable polymeric material located on top of the first layer and the second layer having a predetermined porosity for receiving growth of a second type of tissue dissimilar from the first type of tissue during use; and
   wherein the first and second polymeric materials each have stiffness and compressibility properties corresponding to the first and second types of tissue respectively.

2. The implant as recited in claim 1 wherein at least one of the layers comprises a degradation agent which is adapted to enhance degradation of the polymeric material during use.

3. The implant as recited in claim 1 wherein at least one of the layers comprises a growth factor, a hormone or therapeutic agent to induce, promote or support tissue ingrowth and repair.

4. The implant as recited in claim 2 wherein the degradation agent is incorporated in each of the layers in different amounts in each layer to degrade each polymeric material within different time periods.

5. The implant as recited in claim 1 wherein the first polymeric material has stiffness and compressibility properties substantially comparable to the stiffness and compressibility properties of bone.

6. The implant as recited in claim 1, wherein the second polymeric material has stiffness and compressibility properties substantially comparable to the stiffness and compressibility properties of cartilage.

7. The implant as recited in claim 1 wherein at least one of said polymeric materials comprises a plurality of passages extending into the polymeric material.

8. An implantable molded, biodegradable polymeric tissue support system comprising a two-phase structure comprising a first and second directly adjacent phase:
   wherein the first phase comprises a first porous biodegradable polymeric material, the first phase having a predetermined porosity; and
   the second phase comprises a second porous biodegradable polymeric material, the second phase having a predetermined porosity; and
   wherein the first material and the second material are adapted to be implanted during use into a physiological system at the interface region between a first type of tissue and a second type of tissue, wherein the first and second types of tissue have dissimilar stiffness and compressibility properties, the first and second polymeric materials have dissimilar stiffness and compressibility properties, and the first and second polymeric materials have stiffness and compressibility properties corresponding to the stiffness and compressibility properties of the first and second types of tissue respectively.

9. The system as recited in claim 8 wherein the first phase has stiffness and compressibility properties substantially comparable to the stiffness and compressibility properties of bone.

10. The system as recited in claim 8 wherein the second phase has stiffness and compressibility properties substantially comparable to the stiffness and compressibility properties of cartilage.

11. The system as recited in claim 8 comprising access sites for tissue ingrowth within at least one of the materials comprising passages extending into the material.

12. The implant as recited in claim 2 wherein the degradation agent comprises an enzyme.

13. The implant as recited in claim 1 which is substantially cylinder-shaped.

14. The system of claim 8 wherein the system is substantially cylinder-shaped.

15. The implant as recited in claim 7 wherein the passages have a diameter of about 1.5 mm.

16. The system as recited in claim 11 wherein the passages have a diameter of about 1.5 mm.

17. The implant of claim 1 wherein the pores have a size of about 50–200 micrometers.

18. The system of claim 8 wherein the pores have a size of about 50–200 micrometers.

19. The implant as recited in claim 1 wherein the porosity of each layer is more than 50% of the volume thereof.

20. The system as recited in claim 8 wherein the porosity of each phase is more than 50% of the volume thereof.

* * * * *

UNITED STATES PATENT AND TRADEMARK OFFICE
CERTIFICATE OF CORRECTION

PATENT NO. : 5,607,474

DATED : March 4, 1997

INVENTOR(S) : Athanasiou et al.

It is certified that error appears in the above-identified patent and that said Letters Patent is hereby corrected as shown below:

In the Drawings:

In Figure 1A, please delete reference numeral 14 and the lead line thereto; and

In Figure 1B, please delete reference numeral 16 and the lead line thereto, as shown on the attached page.

Signed and Sealed this

Fifth Day of August, 1997

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO.  : 5,607,474

DATED       : March 4, 1997

INVENTOR(S) : Athanasiou et al.

It is certified that error appears in the above-identified patent and that said Letters Patent is hereby corrected as shown below:

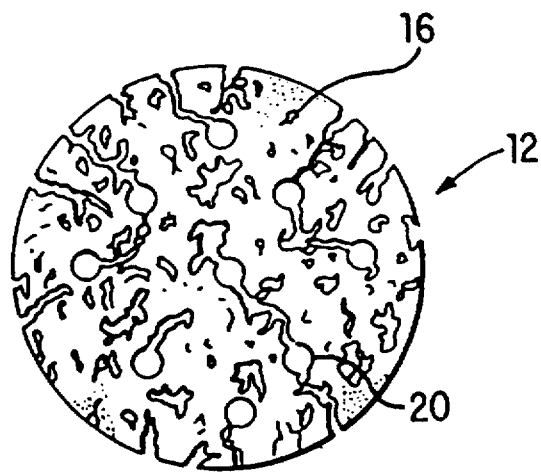

FIG. 1A

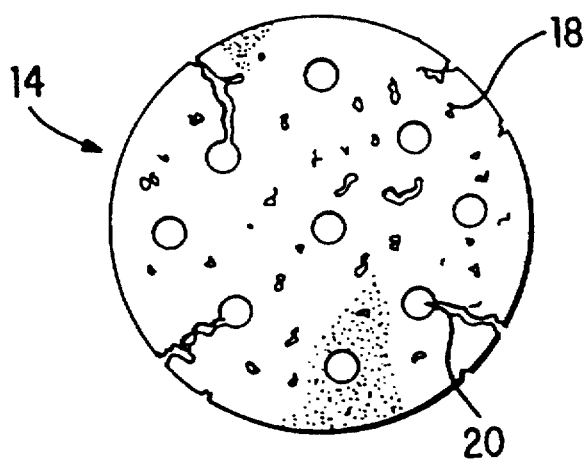

FIG. 1B